US012037406B2

(12) United States Patent
Carpenito et al.

(10) Patent No.: US 12,037,406 B2
(45) Date of Patent: *Jul. 16, 2024

(54) ANTI-CD137 ANTIBODIES FOR COMBINATION WITH ANTI-PD-L1 ANTIBODIES

(71) Applicant: Eli Lilly and Company, Indianapolis, IN (US)

(72) Inventors: Carmine Carpenito, Hartsdale, NY (US); Yiwen Li, Woodcliff, NJ (US)

(73) Assignee: Eli Lilly and Company, Indianapolis, IN (US)

( * ) Notice: Subject to any disclaimer, the term of this patent is extended or adjusted under 35 U.S.C. 154(b) by 200 days.

This patent is subject to a terminal disclaimer.

(21) Appl. No.: 17/040,380

(22) PCT Filed: Mar. 15, 2019

(86) PCT No.: PCT/US2019/022391
§ 371 (c)(1),
(2) Date: Sep. 22, 2020

(87) PCT Pub. No.: WO2019/182878
PCT Pub. Date: Sep. 26, 2019

(65) Prior Publication Data
US 2021/0054088 A1 Feb. 25, 2021

Related U.S. Application Data

(60) Provisional application No. 62/647,016, filed on Mar. 23, 2018.

(51) Int. Cl.
C07K 16/28 (2006.01)
A61K 39/00 (2006.01)
A61K 39/395 (2006.01)
A61K 45/06 (2006.01)
A61N 5/10 (2006.01)
A61P 35/00 (2006.01)

(52) U.S. Cl.
CPC .... C07K 16/2878 (2013.01); A61K 39/39541 (2013.01); A61K 39/39558 (2013.01); A61P 45/06 (2013.01); A61P 35/00 (2018.01); C07K 16/2827 (2013.01); A61K 2039/507 (2013.01); A61N 5/10 (2013.01); C07K 2317/51 (2013.01); C07K 2317/515 (2013.01); C07K 2317/56 (2013.01); C07K 2317/565 (2013.01); C07K 2317/92 (2013.01)

(58) Field of Classification Search
CPC ............ C07K 16/2878; C07K 16/2827; A61K 39/39541; A61K 39/39558
See application file for complete search history.

(56) References Cited

U.S. PATENT DOCUMENTS

| | | | |
|---|---|---|---|
| 6,210,669 B1 | 4/2001 | Aruffo et al. | |
| 6,303,121 B1 | 10/2001 | Kwon | |
| 6,355,779 B1 | 3/2002 | Goodwin et al. | |
| 6,569,997 B1 | 5/2003 | Kwon | |
| 6,974,863 B2 | 12/2005 | Kwon | |
| 7,288,638 B2 | 10/2007 | Jure-Kunkel et al. | |
| 7,651,686 B2 | 1/2010 | Chen et al. | |
| 8,163,550 B2 | 4/2012 | Chen et al. | |
| 8,337,850 B2* | 12/2012 | Ahrens | A61P 35/00 424/139.1 |
| 8,475,790 B2 | 7/2013 | Jure-Kunkel | |
| 8,772,026 B2 | 7/2014 | Chen et al. | |
| 10,214,586 B2* | 2/2019 | Ludwig | A61K 45/06 |
| 10,689,454 B2 | 6/2020 | Ellmark et al. | |
| 10,906,983 B2* | 2/2021 | Frye | C07K 16/2878 |
| 2015/0210769 A1 | 7/2015 | Freeman et al. | |
| 2016/0244528 A1 | 8/2016 | Gray et al. | |
| 2017/0058033 A1* | 3/2017 | Ludwig | C07K 16/2818 |
| 2020/0157234 A1* | 5/2020 | Frye | C07K 16/2878 |
| 2021/0054089 A1* | 2/2021 | Kalos | A61K 45/06 |

FOREIGN PATENT DOCUMENTS

| | | |
|---|---|---|
| WO | 2003049755 A1 | 6/2003 |
| WO | 2015119923 A1 | 8/2015 |
| WO | 2016029073 A2 | 2/2016 |
| WO | 2016034085 A1 | 3/2016 |
| WO | 2017025016 A1 | 2/2017 |
| WO | 2017034916 A1 | 3/2017 |
| WO | 2019027754 A1 | 2/2019 |
| WO | 2019182879 A1 | 9/2019 |
| WO | 2020018354 A1 | 1/2020 |
| WO | 2020092554 A1 | 5/2020 |

OTHER PUBLICATIONS

Perez-Ruiz et al. Anti-CD137 and PD-1/PD-L1 Antibodies En Route toward Clinical Synergy, Clin Cancer Res, 23(18), 5326-5328, Publication Date: Aug. 8, 2017 (Year: 2017).*
Deutscher, M. P. (1990). [8] Maintaining protein stability. In Methods in enzymology (vol. 182, pp. 83-89). Academic Press.
Fisher, T. S., et al. (2012). Targeting of 4-1BB by monoclonal antibody PF-05082566 enhances T-cell function and promotes antitumor activity. Cancer Immunology, Immunotherapy, 61(10), 1721-1733.
International Bureau. International Preliminary Report on Patentability for application PCT/US2019/022391 . . . Mailed Oct. 8, 2020. 8 pages.
International Searching Authority. International Search Report and Written Opinion for application PCT/US2019/022391. Mailed on May 17, 2019. 16 pages.
McCoy, A. J., et al. (2007). Phaser crystallographic software. Journal of applied crystallography, 40(4), 658-674.

(Continued)

Primary Examiner — Peter J Reddig
Assistant Examiner — Cheng Lu
(74) Attorney, Agent, or Firm — Quarles & Brady LLP

(57) ABSTRACT

The present invention relates to antibodies that bind to human CD137 and display agonist activity, and may be useful for treating solid and hematological tumors alone and in combination with anti-human PD-L1 antibodies, chemotherapy, and ionizing radiation.

13 Claims, No Drawings

Specification includes a Sequence Listing.

(56) References Cited

OTHER PUBLICATIONS

Melero, I., et al. (1997). Monoclonal antibodies against the 4-1BB T-cell activation molecule eradicate established tumors. Nature medicine, 3(6), 682-685.
Murshudov, G. N., et al. (2011). REFMAC5 for the refinement of macromolecular crystal structures. Acta Crystallographica Section D: Biological Crystallography, 67(4), 355-367.
North, B. et al., "A New Clustering of Antibody CDR Loop Conformations", Journal of Molecular Biology, 406, 228-256 (2011).
Perez-Ruiz, E., et al. "Anti-CD137 and PD-1/PD-L1 antibodies en route toward clinical synergy." Clinical Cancer Research 23.18 (2017): 5326-5328.
Segal, N. H., et al. "Results from an integrated safety analysis of urelumab, an agonist anti-CD137 monoclonal antibody." Clinical Cancer Research 23.8 (2017): 1929-1936.
Winn, M. D., et al. "Overview of the CCP4 suite and current developments." Acta Crystallographica Section D: Biological Crystallography 67.Pt 4 (2011): 235.
Wei, et al., Combinatorial PD-1 blockade and CD 137 activation has therapeutic efficacy in murine cancer models and synergizes with cisplatin. PLoS One. Dec. 19, 2013;8(12):e84927.
EA 202092265—Office Action dated Sep. 19, 2022.
Azuma, T. et al., "Combination therapy with anti-CD137 and anti-PD-L1 antibodies against renal cell carcinoma," European Urology Supplements, 2014, vol. 13, No. 1.
Chester et al. "Immunotherapy targeting 4-1BB: mechanistic rationale, clinical results, and future strategies" Blood, 2018, 131 (1), 49-57.
Tolcher et al. "Phase Ib Study of Utomilumab (PF-05082566), a 4-1BB/CD137 Agonist, in Combination with Pembrolizumab (MK-3475) in Patients with Advanced Solid Tumors" Clin Cancer Res, 2017, 23(18), 5349-5357.
Emsley, P., et al. "Features and development of Coot." Acta Crystallographica Section D: Biological Crystallography 66.4 (2010): 486-501.
Mcgray, A.J.R., et al. "Combined vaccination and immunostimulatory antibodies provides durable cure of murine melanoma and induces transcriptional changes associated with positive outcome in human melanoma patients." Oncoimmunology 1.4 (2012): 419-431.
Robinson, J. L., et al. "Effects of anti-PD-1 and anti-4-1BB antibody treatment on melanoma-specific T cells in a murine model of melanoma." (2013): 3973-3973.
Verbrugge, I., et al. "Radiotherapy increases the permissiveness of established mammary tumors to rejection by immunomodulatory antibodies." Cancer research 72.13 (2012): 3163-3174.
Guo, Z. et al., "Combined TIM-3 blockade and CD137 activation affords for the long-term protection in a murine model of ovarian cancer," Journal of Translational Medicine 2013, 11(1):215, 11 pages.
Bio X Cell, Catalog #BE0169, Anti-mouse 4-1bb antibody BE0169, Retrieved online: <URL:https://bxcell.com/product/m-cd137/>. [retrieved Aug. 24, 2022], 2022.
Kunik et al., "Structural consensus among antibodies defines the antigen binding site," PLoS Comput. Biol. 2012, 8 (2), e1002388.
MacCallum et al., "Antibody-antigen interactions: contract analysis and binding site topography," J. Mol. Biol. 1996, 262:732-745.
Hurtado et al., "Signals through 4-1BB are costimulatory to previously activated splenic T cells and inhibit activation-induced cell death," J Immunol 1997, 158 (6), pp. 2600-2609.
Kotanides et al., "Characterization of 7A5: A Human CD137 (4-1BB) Receptor Binding Monoclonal Antibody with Differential Agonist Properties That Promotes Antitumor Immunity." Mol Cancer Ther. 2020, 19(4), pp. 988-998.
Kwon et al., "4-1BB: Still in the midst of darkness," Molecules and Cells; Seoul, 2000, vol. 10, Iss. 2, pp. 119-126.
Kwon et al., "cDNA sequences of two inducible T-cell genes," Proc Natl Acad Sci U S A. 1989, 86(6): pp. 1963-1967.
Li et al., "Limited cross-linking of 4-1BB by 4-1BB ligand and the agonist monoclonal antibody utomilumab," Cell Reports, 2018, 25, pp. 909-920.
Shuford et al. , "4-1BB costimulatory signals preferentially induce CD8+ T cell proliferation and lead to the amplification in vivo of cytotoxic T cell responses," J Exp Med. 1997;186(1):47-55.

\* cited by examiner

ANTI-CD137 ANTIBODIES FOR COMBINATION WITH ANTI-PD-L1 ANTIBODIES

CROSS-REFERENCE TO RELATED PATENT APPLICATIONS

The present application is the U.S. National Stage of International Patent Application No. PCT/US2019/022391 filed on Mar. 15, 2019, which claims the benefit of priority under 35 U.S.C. § 119(e) to U.S. Provisional Patent Application No. 62/647,016 filed on Mar. 23, 2018, the contents of both of which are incorporated herein by reference in their entireties.

The present invention is in the field of medicine. Particularly, the present invention relates to agonistic antibodies directed to human CD137 (SEQ ID NO: 1) that can be combined with antibodies directed to human PD-L1 (SEQ ID NO: 26), combinations of compositions comprising such agonistic anti-human CD137 antibodies or anti-human PD-L1 antibodies, and methods of using such agonistic anti-human CD137 antibodies in combination with anti-human PD-L1 antibodies for the treatment of solid and hematological tumors alone or in combination with chemotherapy and other cancer therapeutics.

Tumor cells escape detection and elimination by the immune system through multiple mechanisms some of which include the manipulation of immune checkpoint pathways. Immune checkpoint pathways are used in self-tolerance maintenance and in the regulation of T cell activation, but cancer cells can manipulate these pathways to prolong tumor survival. The programmed cell death 1 (PD-1)/human programmed cell death 1 ligand 1 (PD-L1) pathway is one such immune checkpoint. Human PD-1 is expressed on T cells, and the binding of PD-L1 or PD-L2 to PD-1 has been shown to inhibit T cell proliferation and cytokine production. Moreover, some tumors are known to express PD-L1 and PD-L2 and such expression can contribute to the inhibition of the intratumoral immune response. It has also been shown that some patients develop adaptive resistance to anti-PD-L1 treatment while some do not respond at all.

It is now known that boosting the anti-tumor immune response can be an effective means of cancer therapy. In this regard, CD137, also known as 4-1BB, belongs to the TNF receptor family and plays a role in the activation of T cell immune responses such as by driving T cell proliferation and effector functions, inhibiting activation-induced cell death, and promoting immunological memory. Agonistic antibodies targeting CD137 have shown promise in murine tumor models as a monotherapy (Melero. I. et al., *Nat. Med.* (1997) 3(6):682-685); however, agonist antibodies targeting human CD137 have not yet demonstrated sufficient responses as a monotherapy or combination therapy in human patients. In this regard, neither utomilumab (a human CD137 agonist IgG2 mAb) (Fisher, T. M. et al, *Cancer Immunol. Immunother.* (2012) 61:1721-1733) nor urelumab (a humanized CD137 agonist IgG4 mAb) (Segal, N. H. *Clin. Cancer Res.* (2017) 23(8):1929-1936) have received regulatory approvals for use as a monotherapy or as a combination therapy with anti-PD-L1 antibodies. Indeed, no agonistic antibody targeting human CD137 has been approved for therapeutic use in humans.

Despite the lack of regulatory approvals, the combination of utomilumab and avelumab is being investigated in patients with advanced malignancies (NCT03217747). However, there still exists a need for improved human antibodies that agonize the human CD137 receptor and promote a robust anti-cancer immune response, display acceptable toxicity profiles, and can be combined with anti-human PD-L1 antibody therapies.

Additionally, the use of the previously disclosed agonistic antibodies targeting CD137 as a cancer monotherapy and/or combination agent may be hampered by factors such as the agonistic strength of said antibodies and/or the immune-related adverse events that result from their use at the higher doses likely required for efficacy. In particular, previously disclosed antibodies are either too potent, leading to adverse events, or display sub-optimal efficacy, limiting their combinability with anti-PD-L1 antibody therapies. Described herein are novel human antibodies that agonize the human CD137 receptor, and possess an improved combination of advantageous pharmacological attributes. In particular the anti-human CD137 agonistic antibodies described herein are engineered human, Fcγ-receptor-mediated effector null antibodies that bind human CD137 and cynomolgus monkey CD137, stimulate T cell activation in vitro, promote human CD137 cell surface expression, enhance NF-kappa B activity, inhibit tumor growth in murine tumor models of non-small cell lung cancer as a monotherapy, inhibit T-regulatory cell mediated suppression in vitro, activate desirable immune gene signatures, increase the frequency of intratumoral $CD3^+$ T cells, compete with human CD137-Ligand for binding to human CD137, and bind to unique amino acid residues on human CD137. In this regard, the agonistic antibodies targeting CD137 disclosed herein provide a benefit when combined with an anti-human PD-L1 antibody in murine tumor models.

Non-limiting examples of known anti-human PD-L1 antibodies for use in the combinations of the present invention include atezolizumab, durvalumab, avelumab, BMS-936559, and Antibody B (previously described in WO2017/034916). In some examples, Antibody B comprises a heavy chain variable region having the amino acid sequence of SEQ ID NO: 22 and a light chain variable region having the amino acid sequence of SEQ ID NO: 23. In some examples, Antibody B comprises a heavy chain having the amino acid sequence of SEQ ID NO: 24 and a light chain having the amino acid sequence of SEQ ID NO: 25.

Non-limiting examples of useful chemotherapeutic agents for use in the combinations described herein include 5-fluorouracil, hydroxyurea, gemcitabine, methotrexate, doxorubicin, etoposide, carboplatin, cisplatin, cyclophosphamide, melphalan, dacarbazine, taxol, camptothecin, FOLFIRI, FOLFOX, docetaxel, daunorubicin, paclitaxel, oxaliplatin, and combinations thereof.

The term "antibody" as used herein refers to a polypeptide complex having two heavy chains (HC) and two light chains (LC) such that the heavy chains and lights chains are interconnected by disulfide bonds; wherein the antibody is an IgG subclass antibody.

The CD137 agonist antibodies for use in the present invention are an engineered, non-naturally occurring polypeptide complex. A DNA molecule of the present invention is a DNA molecule that comprises a non-naturally occurring polynucleotide sequence encoding a polypeptide having the amino acid sequence of at least one of the polypeptides in an antibody of the present invention.

The anti-human CD137 antibodies of the present invention are IgG type antibodies and have "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the anti-human CD137 antibodies described herein contain an Fc portion that is derived from human IgG1. IgG1 is well known to bind to the proteins of the Fc-gamma receptor family (FcγR) as well as C1q. Interaction with these receptors can induce antibody-dependent cell cytotoxicity (ADCC) and complement-dependent cytotoxicity (CDC). Therefore, optionally, the anti-human CD137 antibodies described herein are human monoclonal antibodies lacking Fc effector function (IgG1, Fc-null). To achieve an Fc-null IgG1 antibody, selective mutagenesis of residues is necessary within the CH2 region of its IgG1 Fc region. Amino acid substitutions L234A, L235E, and G237A are introduced into IgG1 Fc to reduce binding to FcγRI, FcγRIIa, and FcγRIII, and substitutions A330S and P331S are introduced to reduce C1q-mediated complement fixation. To reduce the potential induction of an immune response when dosed in humans, certain amino acids may require back-mutations to match antibody germline sequences.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. For the purposes of the present invention, the North CDR definitions are used. The North CDR definition (North et al., "A New Clustering of Antibody CDR Loop Conformations", Journal of Molecular Biology, 406, 228-256 (2011)) is based on affinity propagation clustering with a large number of crystal structures.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. Preferably, for anti-human CD137 antibodies of the present invention, the light chain constant region is a kappa constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibodies described herein may readily be produced in mammalian cells, non-limiting examples of which include CHO, NS0, HEK293 and COS cells. The host cells may be cultured using techniques well known in the art. The vectors containing the polynucleotide sequences of interest (e.g., the polynucleotides encoding the polypeptides of the antibody and expression control sequences) can be transferred into the host cell by well-known methods, which may vary depending on the type of cellular host.

Various methods of protein purification may be employed and such methods are known in the art and described, for example, in Deutscher, Methods *in Enzymology* 182: 83-89 (1990) and Scopes, *Protein Purification: Principles and Practice,* 3rd Edition, Springer, NY (1994).

In other embodiments of the present invention, the antibody, or the nucleic acids encoding the same, are provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes, a non-limiting example of which is intravenous administration. An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy,* $22^{nd}$ ed. (2012), A. Loyd et al., Pharmaceutical Press) and comprise an antibody, as disclosed herein, and one or more pharmaceutically acceptable carriers, diluents, or excipients.

Dosing schedules, for intravenous (i.v.) or non-intravenous administration, localized or systemic, or combinations thereof, will typically range from a single bolus dosage or continuous infusion to multiple administrations per day (e.g., every 4-6 hours), or as indicated by the treating physician and the patient's condition. Dosing amounts and frequencies may be determined by the physicians treating the patient.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human CD137 antibody comprises a heavy chain variable region having the amino acid sequence of SEQ ID NO: 8 and a light chain variable region having the amino acid sequence of SEQ ID NO: 9.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human CD137 antibody comprises a heavy chain variable region having the amino acid sequence of SEQ ID NO: 8 and a light chain variable region having the amino acid sequence of SEQ ID NO: 12.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human CD137 antibody comprises a heavy chain having the amino acid sequence of SEQ ID NO: 10 and a light chain having the amino acid sequence of SEQ ID NO: 11.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; and/or wherein the anti-human CD137 antibody comprises a heavy chain having the amino acid sequence of SEQ ID NO: 10 and a light chain having the amino acid sequence of SEQ ID NO: 13.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-L1 antibody is atezolizumab, durvalumab, or avelumab.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-L1 antibody comprises a heavy chain variable region having the amino acid sequence of SEQ ID NO: 22 and a light chain variable region having the amino acid sequence of SEQ ID NO: 23.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-L1 antibody comprises a heavy chain having the amino acid sequence of SEQ ID NO: 24 and a light chain having the amino acid sequence of SEQ ID NO: 25.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is cholangiocarcinoma, head and neck squamous cell carcinoma, lung adenocarcinoma, lung squamous cell carcinoma, or clear cell renal carcinoma.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is bladder cancer, head and neck squamous cell carcinoma, or renal cell carcinoma.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein at least one of the anti-human CD137 antibody and anti-human PD-L1 antibody is administered in combination with ionizing radiation.

The present disclosure provides a method of treating cancer comprising administering to a patient in need thereof an effective amount of an anti-human CD137 (SEQ ID NO: 1) antibody in combination with an effective amount of an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein at least one of the anti-human CD137 antibody and anti-human PD-L1 antibody is administered in combination with one or more chemotherapeutic agents.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human CD137 antibody comprises a heavy chain variable region having the amino acid sequence of SEQ ID NO: 8 and a light chain variable region having the amino acid sequence of SEQ ID NO: 9.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human CD137 antibody comprises a heavy chain variable region having the amino acid sequence of SEQ ID NO: 8 and a light chain variable region having the amino acid sequence of SEQ ID NO: 12.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human CD137 antibody comprises a heavy chain having the amino acid sequence of SEQ ID NO: 10 and a light chain having the amino acid sequence of SEQ ID NO: 11.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human CD137 antibody comprises a heavy chain having the amino acid sequence of SEQ ID NO: 10 and a light chain having the amino acid sequence of SEQ ID NO: 13.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-L1 antibody is atezolizumab, durvalumab, or avelumab.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-L1 antibody comprises a heavy chain variable region having the amino acid sequence of SEQ ID NO: 22 and a light chain variable region having the amino acid sequence of SEQ ID NO: 23.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-L1 antibody comprises a heavy chain having the amino acid sequence of SEQ ID NO: 24 and a light chain having the amino acid sequence of SEQ ID NO: 25.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is cholangiocarcinoma, head and neck squamous cell carcinoma, lung adenocarcinoma, lung squamous cell carcinoma, or clear cell renal carcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is bladder cancer, head and neck squamous cell carcinoma, or renal cell carcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein at least one of the anti-human CD137 antibody and anti-human PD-L1 antibody is administered in combination with ionizing radiation.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein at least one of the anti-human CD137 antibody and anti-human PD-L1 antibody is administered in combination with one or more chemotherapeutic agents.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the anti-human CD137 antibody comprises a heavy chain variable region having the amino acid sequence of SEQ ID NO: 8 and a light chain variable region having the amino acid sequence of SEQ ID NO: 9.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the anti-human CD137 antibody comprises a heavy chain variable region having the amino acid sequence of SEQ ID NO: 8 and a light chain variable region having the amino acid sequence of SEQ ID NO: 12.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the anti-human CD137 antibody comprises a heavy chain having the amino acid sequence of SEQ ID NO: 10 and a light chain having the amino acid sequence of SEQ ID NO: 11.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the anti-human CD137 antibody comprises a heavy chain having the amino acid sequence of SEQ ID NO: 10 and a light chain having the amino acid sequence of SEQ ID NO: 13.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the anti-human PD-L1 antibody is atezolizumab, durvalumab, or avelumab.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the anti-human PD-L1 antibody comprises a heavy chain variable region having the amino acid sequence of SEQ ID NO: 22 and a light chain variable region having the amino acid sequence of SEQ ID NO: 23.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the anti-human PD-L1 antibody comprises a heavy chain having the amino acid sequence of SEQ ID NO: 24 and a light chain having the amino acid sequence of SEQ ID NO: 25.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the cancer is cholangiocarcinoma, head and neck squamous cell carcinoma, lung adenocarcinoma, lung squamous cell carcinoma, or clear cell renal carcinoma.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein the cancer is bladder cancer, head and neck squamous cell carcinoma, or renal cell carcinoma.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein at least one of the anti-human CD137 antibody and anti-human PD-L1 antibody is administered in combination with ionizing radiation.

The present disclosure provides the use of an anti-human CD137 (SEQ ID NO:1) antibody for the manufacture of a medicament for the treatment of cancer, wherein the medicament is to be administered simultaneously, separately, or sequentially with an anti-human PD-L1 (SEQ ID NO: 26) antibody; wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO:5, LCDR2 having the amino acid sequence of SEQ ID NO:6, and LCDR3 having the amino acid sequence of SEQ ID NO:7; wherein at least one of the anti-human CD137 antibody and anti-human PD-L1 antibody is administered in combination with one or more chemotherapeutic agents.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is bladder cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is biliary tract cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is colon cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is endometrial cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is esophageal cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is gastric cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is head and neck cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is non-small cell lung cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is prostate cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is rectal cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is thyroid cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is cholangiocarcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is head and neck squamous cell carcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is lung adenocarcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is lung squamous cell carcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is clear cell renal carcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is bladder cancer.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is head and neck squamous cell carcinoma.

The present disclosure provides an anti-human CD137 (SEQ ID NO: 1) antibody for use in simultaneous, separate, or sequential combination with an anti-human PD-L1 (SEQ ID NO: 26) antibody in the treatment of cancer, wherein the anti-human CD137 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the cancer is renal cell carcinoma.

ANTIBODY CHARACTERIZATION, GENERATION, EXPRESSION, AND PURIFICATION

Antibody production using the heavy chain polynucleotide sequence shown in SEQ ID NO: 14, and the light chain polynucleotide sequence shown in SEQ ID NO: 17 in mammalian cells results in the production of two antibody product-related species: (a) a full length antibody (hereafter referred to as "Antibody A1") having the heavy chain amino acid sequence shown in SEQ ID NO: 10 and the light chain amino acid sequence of SEQ ID NO: 11; and (b) a single amino acid truncated form of the antibody (hereafter referred to as "Antibody A2") resulting from the clipping of the n-terminal alanine of the light chain, the Antibody A2 having the heavy chain amino acid sequence shown in SEQ ID NO: 10 and the light chain amino acid sequence shown in SEQ ID NO: 13. As used herein, "Antibody A1/2" refers to the antibody product that results from the use of the light chain polynucleotide sequence shown in SEQ ID NO: 17 and includes a combination of Antibody A1 (~6%) and Antibody A2 (~94%). Antibody A1 can be synthesized without significant quantities of Antibody A2 using the heavy chain polynucleotide sequence shown in SEQ ID NO: 14 and the light chain polynucleotide sequence shown in SEQ ID NO: 15. Antibody A2 can be synthesized without significant quantities of Antibody A1 using the heavy chain polynucleotide sequence shown in SEQ ID NO: 14 and the light chain polynucleotide sequence shown in SEQ ID NO: 16.

The antibodies of the present invention may be generated by using known methods, including but not limited to, phage display. Additionally, the antibodies derived as described above may be further screened using the assays described herein.

The polypeptides of the variable regions of the heavy chain and light chain and the complete heavy chain and light chain amino acid sequences of Antibodies A1, A2, and B, and the nucleotide sequences encoding the same, are listed in the section entitled "Amino Acid and Nucleotide Sequences." In addition, the SEQ ID NOs for the light chain, heavy chain, light chain variable region, and heavy chain variable region of Antibodies A1, A2, A1/2, and B are shown in Tables 1 & 2.

TABLE 1

| | Corresponding SEQ ID (Amino Acid) | | |
|---|---|---|---|
| | Antibody A1 | Antibody A2 | Antibody B |
| Target | Human CD137 | Human CD137 | Human PD-L1 |
| HCDR1 | 2 | 2 | — |
| HCDR2 | 3 | 3 | — |
| HCDR3 | 4 | 4 | — |
| LCDR1 | 5 | 5 | — |
| LCDR2 | 6 | 6 | — |
| LCDR3 | 7 | 7 | — |
| HCVR | 8 | 8 | 22 |
| LCVR | 9 | 12 | 23 |
| Heavy chain | 10 | 10 | 24 |
| Light chain | 11 | 13 | 25 |

TABLE 2

| | Corresponding SEQ ID (DNA) | | |
|---|---|---|---|
| | Antibody A1 | Antibody A2 | Antibody A1/2 |
| HC | 14 | 14 | 14 |
| LC | 15 | 16 | 17 |

The antibodies of the present invention, including, but not limited to, Antibodies A1, A2, A1/2, and B can be made and purified essentially as follows. An appropriate host cell, such as HEK 293 or CHO, can be either transiently or stably transfected with an expression system for secreting antibodies using an optimal predetermined HC:LC vector ratio or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare), that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The product may be immediately frozen at −70° C. or may be lyophilized.

As used herein, BMS20H4.9 refers to an antibody having the heavy chain shown in SEQ ID NO: 18 and the light chain shown in SEQ ID NO: 19, and has been previously described in U.S. Pat. No. 7,288,638. As used herein, PF83 refers to an antibody having the heavy chain shown in SEQ ID NO: 20 and the light chain shown in SEQ ID NO: 21, and has been previously described in U.S. Pat. No. 8,337,850.

Antibody A1/2 Binds to Human CD137

The ability of the antibodies disclosed herein to bind human CD137 can be measured by ELISA. To measure binding to human CD137, a 96-well plate (Nunc) is coated with human CD137-Fc (R&D Systems) overnight at 4° C. Wells are blocked for 2 h with blocking buffer (PBS containing 0.2% bovine serum albumin and 0.05% Tween-20). Wells are washed three times with PBS containing 0.05% Tween-20. Antibody A1/2 or control IgG (100 microliters) is then added at different concentrations and incubated at room temperature for 1 h. After washing, the plate is incubated with 100 microliters of goat anti-human IgG F(ab')2-HRP conjugate (Jackson Immuno Research Laboratories) at room temperature for 45 minutes. The plates are washed and then incubated with 100 microliters of 3,3', 5,5'-tetra-methylbenzidine. The absorbance at 650 nm is read on a SpectraMax® microplate reader. The half maximal effective concentration ($EC_{50}$) is calculated using GraphPad Prism 7 software.

In experiments performed essentially as described above, Antibody A1/2 binds human CD137 with an $EC_{50}$ of 0.027 nM.

Antibody A1/2 Binds to Cynomolgus Monkey CD137

The ability of the antibodies disclosed herein to bind to cell surface cynomolgus monkey CD137 can be measured using a flow cytometric assay. Cynomolgus monkey CD137 expressing stable cells are generated by transfecting Cyno-CD137 receptor plasmid DNA into human 293 cells (ATCC) using Lipofectamine™ 2000 reagent (Invitrogen™) per manufacturer's protocol. Stable cells are selected using 0.5 micrograms/mL puromycin in Dulbecoo's Modified Eagle's Medium containing 10% fetal bovine serum and 1% GlutaMAX™. For flow cytometry, confluent adherent cells are detached using Gibco® Cell Dissociation Buffer (Life Technologies), blocked in FACS buffer (phosphate buffered saline containing 3% fetal bovine serum) for 1 h at 4° C., and then transferred into a 96-well round-bottom plate at a density of $1 \times 10^5$ cells/well. Antibody A1/2, BMS20H4.9, PF83, or control human IgG1 (diluted in FACS buffer 1:4 starting at 0.5 micrograms/mL) are added (100 microliters) and cells are stained for 1 h at 4° C.

After washing in FACS buffer, secondary antibody R-phycoerythrin conjugated goat anti-human IgG, $F(ab')_2$ fragment specific antibody (Jackson ImmunoResearch Laboratories) is added at a 1:200 dilution and cells are incubated at 4° C. for 30 minutes. Cells are washed and live/dead cell staining is performed using LIVE/DEAD® Fixable Far Red Dead Cell Stain kit (Life Technologies) per manufacturer's protocol. Cells are washed in FACS buffer and processed on an IntelliCyt HTFC® Screening System. Flow cytometry data is analyzed using FlowJo® Software. Mean fluorescence intensity (MFI) ratio is calculated as the (MFI of Experimental antibody)/(MFI of the control IgG).

In experiments performed essentially as described above, Antibody A1/2 at a concentration of 0.5 micrograms/mL displays a higher MFI ratio of 153 as compared to BMS20H4.9 (MFI ratio of 0.94) and PF83 (MFI ratio of 37).

Antibody A1/2 Binding on Human Cells Increases CD137 Expression

The ability of the antibodies disclosed herein to modulate human CD137 cell surface levels can be determined as follows. Human CD137 expressing stable cells are generated by transfecting human CD137 plasmid DNA into human 293 cells (ATCC) using Lipofectamine™ 2000 reagent (Invitrogen™) per manufacturer's protocol. Stable cells are selected using 0.5 micrograms/mL of puromycin in Dulbecoo's Modified Eagle's Medium containing 10% fetal bovine serum and 1% GlutaMAX™. CD137 antibodies starting at 300 nanomolar in media are incubated with the cells at 37° C. for 24 hr. The cells are washed with PBS, detached using Gibco® Cell Dissociation Buffer, and stained with the same CD137 antibodies in cold buffer (1x PBS, 1% BSA, 0.09% sodium azide) for 2 h. After washing, cells are stained with Alexa Fluor 647-conjugated goat anti-human IgG detection antibody (Jackson ImmunoResearch Laboratories) for 30 minutes. Cells are washed and differentially labeled with Zombie Green Live/Dead (BioLegend) per manufacturer's protocol. All cells are processed on a Fortessa X-20. Analysis is performed with FlowJo® Software to generate Median Fluorescence Intensity (MFI) of Alexa Fluor 647 and calibrated to an Alexa Fluor 647 molecules of equivalent soluble fluorochrome (MESF) standard curve (Bangs Laboratories). MESF values are normalized to untreated stained controls (100%) and untreated isotype stained controls (0%).

In experiments performed essentially as described above, Antibody A1/2 at a concentration of 300 nanomolar induces an increase (21%) in CD137 levels compared to PF83 (12%) whereas BMS20H4.9 reduces CD137 on the cell surface by 56%.

NF-kappaB Luciferase Reporter Assay Activity of Antibody A1/2

The ability of the antibodies disclosed herein to activate NF-kappaB can be measured as follows. Double stable NF-kappaB luciferase reporter/human CD137-293 cells are generated by transfecting pGL4.32[luc2P/NF-kappaB-RE/Hygro] plasmid DNA (Promega) into human CD137-expressing 293 cells using Lipofectamine™ 2000 Reagent (Life Technologies) per manufacturer's protocol. Stable cells are selected using 100 micrograms/mL hygromycin and 0.5 micrograms/mL puromycin in Dulbecoo's Modified Eagle's Medium containing 10% fetal bovine serum and 1% GlutaMAX™. Cells are plated in a 384 well plate at a density of $5 \times 10^3$ cells/well using the Thermo MultiDrop Combi Reagent Dispenser (Thermo Fisher Scientific) and cultured overnight at 37° C. Antibody A1/2, BMS20H4.9, PF83, or control human IgG1 are diluted in phosphate buffered saline (PBS) using Hamilton STAR™ (Hamilton Company) at 10-point 2-fold dilutions within the plate starting at 9 micromolar or 1.33 micromolar and transferred to cells. Cells are then incubated with the antibodies for 5.5 h at 37° C. in 5% $CO_2$ and then processed using the ONE-Glo™ Luciferase Assay System (Promega™) and Thermo™ Scientific MultiDrop™ Combi Reagent Dispenser. Luminescence is measured using a SpectraMax® microplate reader (Molecular Devices) and data analysis is performed using a Genedata Screener® (Genedata). Data is normalized as follows: % Activity=[(Well Value-Median of Minimum Control)/(Median of Maximum Control-Median of Minimum Control)]×100%.

In experiments performed essentially as described above, Antibody A1/2 displays a max activity of 78% that is higher than PF83 (max activity of 12%) and lower than BMS20H4.9 (max activity of 115%).

Antibody A1/2 Promotes T Cell-Derived Interferon-Gamma Production

The ability of the antibodies disclosed herein to promote T cell-derived interferon-gamma (IFN-gamma) production can be measured as follows. Human peripheral blood mononuclear cells (PBMCs) are isolated from whole blood or leukopacs by Ficoll density gradient centrifugation (Ficoll® Paque PLUS; GE Healthcare) and grown in Roswell Park Memorial Institute medium (RPMI) (Life Technologies) with 10% fetal calf serum (HyClone). Anti-human CD3 antibody clone HIT3a (BD Biosciences) in PBS is coated onto a 96-well plate (typical range: 2 to 15 nanograms/well) and incubated overnight at 4° C. After aspirating, wells are rinsed with PBS and human PBMCs are transferred onto a 96-well plate at a density of $1.5 \times 10^5$ cells/well. Antibody A1/2, BMS20H4.9, PF83, or control human IgG1 are prepared by diluting 1:4 in RPMI containing 10% fetal bovine serum at a starting concentration of 80 micrograms/mL. Anti-human CD28 antibody clone CD28.2 (BioLegend) is added to the plate (typical range 0.2 to 2 micrograms/mL) followed by the test antibody and incubated for 96 h at 37° C. in a humidified 5% $CO_2$ incubator. Supernatants are collected and human IFN-gamma levels are measured using a R&D Systems® human IFN-gamma DuoSet ELISA Kit. Briefly, IFN-gamma capture antibody is coated onto plate (4 micrograms/mL) overnight at room temperature. After aspirating and washing, the plate is blocked for 1 h at room temperature. Sample supernatants and IFN-gamma standard are added and incubated for 2 h at room temperature. After washing, 100 microliters of IFN-gamma detection antibody is added, incubated for 2 hr at room temperature, and washed. Streptavidin-HRP (100 microliters of 1:40 dilution) is added for 20 minutes at room temperature. After washing, plates are developed by adding 100 microliters substrate solution for 20 minutes followed by 50 microliters stop solution, and the signal is measured at 450 nm with SpectraMax® microplate reader. Data analysis is performed using SoftMax Pro software and GraphPad Prism (GraphPad Software). Fold induction is calculated as sample mean IFN-gamma (pg/mL)/Control hIgG1 mean IFN-gamma (pg/mL).

In experiments performed essentially as described above, Antibody A1/2 enhances the sub-optimal activation of human PBMCs by CD3/CD28 co-stimulation as measured by IFN-gamma cytokine production. In this regard, treatment with Antibody A1/2 at 5 micrograms/ml results in a 3.8-fold increase in the production of IFN-gamma that was higher than PF83 (1.6-fold increase) and lower than BMS20H4.9 (9.4-fold increase).

Antibody A1/2 Solid-Phase Binding Assay

The binding of Antibody A1/2 to human C1q can be measured using an ELISA assay. Antibody A1/2 and control antibodies (negative control IgG1) are serially diluted in PBS and coated onto an ELISA plate overnight at 4° C. Human C1q in casein buffer is added at a concentration of 10 milligrams/mL and incubated for 2 hrs. Human C1q is detected by incubating the plates with anti-human C1q-HRP (AbD Serotec Inc., 1:200 dilution) for 1 h and the plate is developed using TMB (KPL, Inc.). Absorbance is measured at 450 nm with Synergy Neo2 hybrid multi-mode reader (BioTek®).

The binding of Antibody A1/2 to FcγRI, FcγRIIa(H), FcγRIIb, FcγRIIIa(F), and FcγRIIIa(V) is determined using an MSD assay (Meso Scale Diagnostics). Briefly, Fcγ receptors are coated onto a Meso Scale plate overnight and serially diluted test antibodies are added to the plate and incubated for 2 h. Antibody A1/2 is detected using an anti-human secondary antibody (Meso Scale Diagnostics, D20TF-6) and the plate is developed with Read Buffer T (Meso Scale Diagnostics, R92TC-1). Luminescence is measured on a SECTOR Imager 2400 (Meso Scale Diagnostics) and data is analyzed using GraphPad Prism 7.0 software.

mouse) are injected subcutaneously into the right flank of female NOD/SCID Gamma (NSG) mice at 7 weeks of age (Jackson Laboratories). When tumors reach approximately 350 mm$^3$ to 450 mm$^3$ in size, mice are randomized into groups of 5 to 8. Human expanded T cells are generated by stimulating naïve human PBMCs with Dynabeads® Human T-expander CD3/CD28 beads (Thermo Fisher Scientific) for 9 to 10 days and banked. Human PBMCs (NY Blood Center) are prepared by centrifugation over Ficoll® Paque PLUS in SepMate tubes (STEMCELL Technologies) and banked. Expanded T cells are thawed and 1×10$^6$ cells are injected into the mice. As a control, tumor cells alone are implanted with no T cells or PBMCs in some mice. Treatment starts at either Day 0 or Day 1. Treatment groups include control IgG, BMS20H4.9, PF83, and Antibody A1/2. Animals are dosed via intraperitoneal injection at 10 mg/kg of antibody once weekly for 4 weeks. Body weight (BW) is recorded twice a week and the percent change in BW is calculated using the formula: (BW on observation day−BW on initial day)/BW initial day×100%. Tumor volumes are measured twice per week using electronic calipers. Tumor volume is calculated using the formula: Tumor Volume (mm$^3$)=π/6*Length*Width$^2$. The % T/C is calculated using the formula 100×ΔT/ΔC if ΔT>0 of the geometric mean values. ΔT=mean tumor volume of the drug-treated group on the observation day of the study−mean tumor volume of the drug-treated group on initial day of dosing; ΔC=mean tumor volume of the control group on the observation day of the study−mean tumor volume of the control group on initial day of dosing. Statistical analysis of tumor volume data is performed by two-way repeated measures analysis of variance by time and treatment using the MIXED procedures in SAS software (Version 9.2).

In experiments performed essentially as described above, mice treated with Antibody A1/2 demonstrated significant tumor growth inhibition (T/C %=30.6; P<0.001) in contrast to mice treated with PF83 (T/C %=81.2) and BMS20H4.9 (T/C %=96.9) which showed no inhibition.

Kinetics/Affinity Results for Antibody A1, Antibody A2, and Antibody A1/2

A Biacore T200 instrument can be used to measure the kinetics of immobilized human CD137-Fc binding to Antibody A1, Antibody A2, and Antibody A1/2. Recombinant human extracellular CD137-Fc protein (R&D Systems) is

TABLE 3

| Antibody | FcγRI (EC$_{50}$ nM) | FcγRIIa(H) (EC$_{50}$ nM) | FcγRIIb (EC$_{50}$ nM) | FcγRIIIa(F) (EC$_{50}$ nM) | FcγRIIIa(V) (EC$_{50}$ nM) | Human C1q (EC$_{50}$ nM) |
|---|---|---|---|---|---|---|
| Antibody A1/2 | >5* | >134* | >134* | >134* | >134* | >330* |
| Positive Control IgG1 (Intact Fc receptor effector functionality) | 0.8 | 93.7 | >134* | 19 | 6.2 | 8.9 |

*Denotes the maximum concentration of the antibody tested

In experiments performed essentially as described above, Antibody A1/2 did not bind to FcγRI, FcγRIIa, FcγRIIb, FcγRIIIa, FcγRIIIa, or C1q (as shown in Table 3 above). In other experiments, Antibody A1/2 exhibited no detectable effector function in cell-based antibody-dependent cellular cytotoxicity and complement-dependent cytotoxicity assays.

Antitumor Efficacy of Antibody A1/2 in an Established Tumor Model

The HCC827 human non-small cell lung cancer (ATCC) tumor cell line is maintained in its respective media and harvested for implantation. Tumor cells (1×10$^7$ cells per covalently immobilized to a CMS sensor chip via amine coupling (GE Healthcare). CD137 antibody testing is performed at a flow rate of 30 microliters/min in HBS-EP+ buffer. Samples are injected at various concentrations and measurements obtained at 25° C. The surface is regenerated after each sample injection with 10 millimolar Glycine-HCl pH2.0 at flow rate of 30 microliters/min for 24 seconds and then stabilized with buffer for 10 seconds. Sensorgrams of concentrations ranging from 0.123 nanomolar to 30 nanomolar are evaluated using Biacore T200 software. Calculation of association (Ka) and dissociation (Kd) rate constants are based on a 1:1 Langmuir binding model fit. The equilibrium dissociation constant (KD) or binding affinity constant is calculated from the ratio of kinetic rate constants Kd/Ka.

In experiments performed essentially as described above, Antibody A1, Antibody A2, and Antibody A1/2 bind to human CD137 with the kinetics and affinity constants illustrated in Table 4.

TABLE 4

| Antibody | $K_{on}$ (1/Ms) | $K_{off}$ (1/s) | $K_D$ (M) | $R_{max}$ | Chi² |
|---|---|---|---|---|---|
| Antibody A2 | 1.33E+06 | 7.13E−03 | 5.36E−09 | 23.10 | 0.247 |
| Antibody A1 | 1.61E+06 | 5.36E−03 | 3.33E−09 | 22.76 | 0.355 |
| Antibody A1/2 | 1.52E+06 | 7.11E−03 | 4.67E−09 | 20.86 | 0.303 |

NF-kappaB Luciferase Reporter Assay Comparing Antibody A1, Antibody A2, and Antibody A1/2

The ability of the antibodies disclosed herein to activate NF-kappaB can be measured as previously described herein with the modification that the antibody dilutions are prepared in PBS and 10-point 2-fold dilutions are made within the plate starting at 9 micromolar.

In experiments performed essentially as described above, Antibody A1/2 (max activity of 70.5%) displayed a similar max activity as compared to Antibody A1 (max activity of 63.4%) and Antibody A2 (max activity of 72.3%).

Antibody A1 and Antibody A2 Promote T Cell-Derived Interferon-Gamma Production

The ability of antibodies disclosed herein to promote T cell-derived interferon-gamma (IFN-gamma) production can be measured as previously described herein. In experiments performed essentially as described herein, Antibody A1, Antibody A2, and Antibody A1/2 enhance the sub-optimal activation of human PBMCs by CD3/CD28 co-stimulation as measured by IFN-gamma cytokine production. In this regard, treatment with Antibody A1/2 at 5 micrograms/mL results in a 3.1-fold increase in the production of IFN-gamma that was comparable to Antibody A1 (3.5-fold increase) and Antibody A2 (3.5-fold increase).

Antitumor Efficacy of Antibody A1 and Antibody A2 in an Established Tumor Model

The ability of the antibodies disclosed herein to inhibit tumor growth in mice can be measured as previously described herein.

In experiments performed as essentially described above, Antibody A1, Antibody A2, and Antibody A1/2 inhibit tumor growth in the HCC827 established tumor model. Treatment with Antibody A1/2 (T/C %=47.1%; P<0.001) shows a similar reduction in tumor growth as Antibody A1 (T/C %=56.0%; P<0.001) and Antibody A2 (T/C %=48.7%; P<0.001).

Epitope of Antibody A1 as Determined Via X-Ray Crystallography

Antibody A1-Fab is purified from a 293HEK cell supernatant using a 12 mL CaptureSelect IgG-CH1 Affinity Matrix. SDS-PAGE and analytical size exclusion chromatography (SEC) are utilized to address the purity and quality of the purified Antibody A1-Fab. The eluted material of this matrix is buffer exchanged with 1× Tris-buffered saline (TBS). The hCD137* (*(human CD137 amino acids 22-161, ΔC121S)-AAA-6His) is purified from a 293HEK supernatant in three steps that utilize Ni Sepharose® Excel columns, Ni-NTA columns, and SEC columns. Briefly, two liters of supernatant is loaded directly without any buffer exchange into a Ni Sepharose Excel column. The elutant of this step is buffer exchanged with PBS and further purified using a Ni-NTA gravity flow column. The elutant of this step is further purified and buffer exchanged with 1×TBS using a preparatory SEC column. Flow through from the first Ni Sepharose Excel step contains significant amounts of hCD137*. It is then reloaded into a Ni Sepharose Excel column followed by the Ni-NTA and preparatory SEC columns. SDS-PAGE is used to pool the hCD137* fractions based on their purity. The concentration of hCD137* is 14.5 milligrams/mL and that of Antibody A1-Fab is 7.5 milligrams/mL.

The Antibody A1-Fab:CD137* complexes are combined at a 1:1 molar ratio and then subjected to a gel filtration column, pre-equilibrated in 20 millimolarTris pH 8.0, 100 millimolar sodium chloride. The resulting complex is concentrated to 12.5 milligrams/mL. After filtration, the Antibody A1-Fab:CD137 complex is set to a 1:1 ratio with sparse matrix crystal screening conditions in sitting drop plates using a Phoenix liquid handler, at both 21° C. and 8° C. Large, prism-like crystals grow in a single condition within 4 days in 1 molar Tri Sodium Citrate pH 6.5 at 21° C. Crystals are harvested and cryo-protected in 20% glycerol and reservoir conditions, mounted and flash-frozen in liquid nitrogen, then using an Advanced Photo Source, Argonne National Laboratory, samples are X-ray screened and the data is collected. The Antibody A1-Fab/hCD137* data is processed to 2.4 Å using the CCP4 suite of programs (Winn, M. D. et al. *Acta. Cryst.* 2011: D67, 235-242). The crystal belongs to Space Group P3121, with cell parameters a=b=124.9 Å, b=112.7 Å, α=β=90° and γ=120°. The structure is determined by Molecular Replacement with the program Phaser (McCoy, A. J. et al. *J. Appl. Cryst.* 2007 40: 658-674) using an internal Fab structure as a search model. The molecular replacement solution for the Fab is refined using Refmac (Winn, M. D. et al. *Acta. Cryst.* 2011: D67, 235-242; Murshudov, G. N. *Act. Cryst.* 2011: D67, 355-367) and Buster (Bricogne, G. et al. 2016; Buster Version 2.11.6. Cambridge, United Kingdom: Global Phasing Let.). Maps from the refinement are used to manually build in the model for CD137 using the program COOT (Emsley, P. Acta Cryst. 2010: D66, 486-501). The refined R-factors are R=17.8%, Rfree=20.5%.

In experiments performed essentially as described in this assay, Antibody A1-Fab:hCD137* complex is resolved and the epitope/paratope is illustrated in Table 5 below. Table 5 lists the residues on Antibody A1-Fab that are within 6 Å of the listed residues on hCD137*. The heavy chain of the Antibody A1-Fab has 57 contacts (cutoff 6 Å) with hCD137* while the light chain has 18 contacts (cutoff 6 Å).

TABLE 5

| Human CD137 (Epitope) | Antibody A1 Heavy Chain (Paratope) | Antibody A1 Light Chain (Paratope) |
|---|---|---|
| S55 | Q62 | — |
| Q59 | Q62 | — |
| D63 | Q62 | — |
| R66 | F55 | — |
| F72 | F55 | — |
| H93 | T103 | — |
| C94 | T102, T103, A104, P105 | — |
| L95 | M101, T102, T103, P105, G106, T107 | — |
| G96 | L100, M101, T102, T103, P105, G106, T107 | G92, N93 |

TABLE 5-continued

| Human CD137 (Epitope) | Antibody A1 Heavy Chain (Paratope) | Antibody A1 Light Chain (Paratope) |
|---|---|---|
| A97 | M101, T102, P105, G106, T107 | G92, N93, S94, F95, L97 |
| G98 | P105 | G92, N93, S94, F95 |
| C99 | P105 | — |
| S100 | I52, F55, N59, M101, P105, T107 | F95 |
| M101 | S31, I52, I54, F55, M101 | — |
| C102 | F55 | — |
| E103 | T103 | — |
| L112 | T103 | — |
| T113 | T103 | — |
| K114 | M101, T102, T103, A104 | D51, D54 |
| K115 | L100, M101, T102, T103, D110 | F50, E56, T57 |
| G116 | M101, T102, T103 | F50 |

Antibody A1/2 Completely Blocks CD137/CD137-Ligand Interactions

The ability of the antibodies disclosed herein to block human CD137 and CD137-Ligand (hereafter, CD137L) interactions can be measured with an ELISA assay. First, an ELISA assay is utilized to quantify the binding $EC_{50}$ of hCD137** (human CD137 amino acids 22-164, ΔC121S)-AAA-FLAG to hCD137L* and Antibody A1/2, BMS20H4.9 and PF83. The wells of a 96 well Immulon® 4HBX ELISA plate are coated overnight with 50 nanograms of hCD137** in 100 microliters of PBS, pH 7.2 with mild agitation at 4° C. After blocking with 5% BSA in PBST and washing, a five-fold dilution series (392 nanomolar-0.005 nanomolar) of His-tagged recombinant human CD137L (hereafter referred to as hCD137L*) (R&D Systems), (53-0.00068 nanomolar) of BMS20H4.9, (107-0.0014 nanomolar) of PF83, or (53-0.00068 nanomolar) of Antibody A1/2 are added with each dilution conducted in duplicate and incubated with mild agitation for 1 h at room temperature. The wells treated with the anti-CD137 antibodies are then washed and a 1:10000 dilution of HRP-conjugated goat anti-Fab antibody (Jackson ImmunoResearch Laboratories) is added and incubated at room temperature following standard protocol. The wells treated with hCD137L* are then washed and a 1:5000 dilution of HRP-conjugated mouse anti-His antibody (Sigma-Aldrich®) is added and the plates are incubated at room temperature following standard protocol. TMB peroxidase chromogenic substrate and stop solution are used according to manufacturer's instruction for visualization and detection of signals. Absorbance readings are plotted in GraphPad Prism Software Version 6. $EC_{50}$ values are calculated by nonlinear regression curve fit analysis of the software's One Site-Specific Binding function. In experiments performed as described, the binding affinities ($EC_{50}$) to hCD137** are determined as 0.6 nanomolar for hCD137L, 1.4 nanomolar for Antibody 1/2, 0.43 nanomolar for BMS20H4.9, and greater than 10 nanomolar for PF83.

The ability of hCD137L* to compete with BMS20H4.9, PF83, and Antibody A1/2 for binding to hCD137 can be determined as follows. A 96-well Immulon 4HBX ELISA plate is coated overnight with 50 nanograms of hCD137 in 100 microliters of PBS, pH 7.2 with mild agitation at 4° C. After blocking (with 5% BSA in PBST) and washing, a five-fold dilution (196 to 0.0025 nanomolar) of hCD137L* is mixed with saturating amounts of the designated antibody: Antibody A1/2 (200 nanograms/well), BMS20H4.9 (3 nanograms/well), or PF83 (1000 nanograms/well). The mixtures are then added to the wells in duplicates and incubated with mild agitation at room temperature for 1 h. After washing, the plate is incubated with HRP-conjugated goat anti-Fab antibody (1:1000 dilutions, Jackson ImmunoResearch Laboratories) at room temperature following standard protocol. TMB peroxidase chromogenic substrate and stop solution are used according to manufacturer's instruction for visualization and detection of signals.

The percentage of mAb that remains bound to CD137 is plotted and $IC_{50}$ values are calculated by nonlinear regression curve fit analysis using GraphPad Prism software. In experiments performed essentially as described above, hCD137L* fully blocks the binding of Antibody A1/2 to hCD137** with an $IC_{50}$ of 0.401 nanomolar. hCD137L* also blocks the binding of PF83 to hCD137** with an $IC_{50}$ of 1.037 nanomolar (30% binding signal remains on the surface). There is no measurable effect of hCD137L* on the binding of BMS20H4.9 to hCD137**.

Antibody A1/2 Binds Human CD137 at Specific Amino Acid Residues that are Distinct from BMS20H4.9 and PF83

Human CD137 point mutations are introduced to determine the amino acids residues where Antibody A1/2, BMS20H4.9, and PF83 bind to human CD137. The CD137-Fc mutants are generated using the standard protocol of a commercially-available site directed mutagenesis kit (Quickchange II kit, Qiagen). The wild-type and mutant CD137-Fc proteins are expressed and purified. All the mutants reported here have a size exclusion profile similar to that of the wild-type CD137-Fc (i.e. the mutations introduced do not compromise the structural integrity of the protein). To determine the impact of a mutation on the binding of the antibodies, a point ELISA assay against CD137-Fc wild type and mutants is utilized. The wells of a 96-well Immulon 4HBX ELISA plate are coated overnight with 50 nanograms of human CD137-ECD-C121S-Fc or its mutants in 100 microliters of PBS, pH 7.2 with mild agitation at 4° C. After blocking (with 5% BSA in PBST) and washing, a five-fold dilution eight-point series (100-0.00128 nanomolar) of the designated antibody is added and incubated with mild agitation at room temperature for 1 h. The wells are washed and a HRP-conjugated secondary antibody (1:10000 dilution of HRP-conjugated goat anti-Fab antibody (Jackson ImmunoResearch Laboratories) is added and incubated at room temperature following standard protocol. TMB peroxidase chromogenic substrate and stop solution are used according to manufacturer's instruction for visualization and detection of signals. Absorbance readings for each concentration point is normalized by the absorbance of the wild-type interaction. For each mutant, the mean of the normalized ratio for the eight concentrations is determined.

Mutations were individually introduced into human CD137 (SEQ ID NO: 1) at positions: P27, N42, D63, Q67, A97, G98, S100, M101, Q104, K114, K115, R130, I132, R134. Table 6 demonstrates the binding profiles of BMS20H4.9 and Antibody A1/2 for the shown mutants of human CD137. Table 7 demonstrates the binding profiles of PF83 and Antibody A1/2 for the shown mutants of human CD137. Collectively, Tables 6 and 7 demonstrate that Antibody A1/2 binds to distinct amino acid residues on human CD137 as compared to BMS20H4.9 and PF-83.

TABLE 6

| | BMS20H4.9<br>(% of binding relative<br>to wild-type hCD137) | Antibody A1/2<br>(% of binding relative<br>to wild-type hCD137) |
|---|---|---|
| P27L* | 85 | 100 |
| N42S* | 0 | 100 |
| D63N | 100 | 100 |
| Q67R | 100 | 100 |
| Q67V | 100 | 100 |
| A97P | 100 | 15 |
| G98K | 100 | 85 |
| G98Q | 100 | 100 |
| S100T | 100 | 100 |
| M101R | 100 | 100 |
| Q104K | 100 | 100 |
| K114E | 100 | 20 |
| K115Q | 100 | 25 |

*Denotes positions that are outside the epitope of Antibody A1/2 as determined via X-Ray Crystallography at 6 Å

TABLE 7

| | Antibody A1/2<br>(% of binding relative<br>to wild-type hCD137) | PF83<br>(% of binding relative<br>to wild-type hCD137) |
|---|---|---|
| K115Q | 25 | 100 |
| R130A* | 100 | 100 |
| R130H* | 100 | 100 |
| I132V* | 100 | 100 |
| R134Q* | 100 | 25 |

*Denotes positions that are outside the epitope of Antibody A1/2 as determined via X-Ray Crystallography at 6 Å.

CD137 Gene Expression in Human Tumors

CD137 gene expression profile in human tumor immune infiltrates can be analyzed using The Cancer Genome Atlas (TCGA) database and computational methodologies. Briefly, expression ratios of CD137/CD3e are generated from Omicsoft curated TCGA RNASeq results. To compare the expression ratios of CD137/CD3e in tumor samples and adjacent normals of same tissue, a t-test is performed and Cohen's d is calculated for each tumor type. Tumor types that have a P value <0.05 in the t-test of expression ratio of tumor versus normal and a large effect size of Cohen's d>0.8 are statistically significant. The difference in expression ratio of CD137/CD3e in tumor versus normal tissue is calculated as the log fold change (log FC).

In experiments performed as described, an increased tumor CD137/CD3 ratio is observed across different cancer types, including, but not limited to, breast, colon, endometrial, bladder and head and neck (Table 8). Tumors enriched with CD137+ lymphocytes are candidates for CD137 antibody therapy using Antibody A1, Antibody A2 or Antibody A1/2.

TABLE 8

| Cancer | CD137/CD3 Expression<br>Ratio (logFC) | P Value |
|---|---|---|
| Bladder | 1.92 | 3.85E−03 |
| Breast | 2.46 | 3.56E−39 |
| Cholangiocarcinoma | 1.78 | 4.81E−06 |
| Colon | 2.36 | 1.23E−19 |
| Endometrial | 2.14 | 4.01E−15 |
| Esophageal | 1.07 | 1.71E−04 |
| Gastric | 1.68 | 9.27E−10 |
| Head & Neck | 1.90 | 8.06E−15 |
| Lung Adenocarcinoma | 1.37 | 2.63E−13 |
| Lung Squamous Cell Carcinoma | 1.63 | 2.37E−13 |
| Prostate | 1.04 | 2.73E−04 |
| Rectal | 1.62 | 1.40E−05 |
| Thyroid | 1.24 | 2.29E−06 |

Antibody A1/2 Increases CD3+ T Cell Tumor Infiltration In Vivo

The ability of antibodies disclosed herein to alter T cell tumor infiltration in humanized mouse models can be determined by immunohistochemistry (IHC). Briefly, L55 human non-small cell lung cancer cells (L55-CBG-2A-GFP, University of Pennsylvania) are implanted in NSG mice. When tumors reach 250-300 mm$^3$-in size, human PBMCs ($8\times10^6$ cells) are injected and antibodies are dosed at 10 milligrams/kg once weekly for 4 weeks. At the end of the study, tumors are collected in formalin, processed into paraffin, sectioned, and stained with an anti-CD3 antibody (Cell Signaling Technology). Images are acquired at 200× magnification using an Aperio XT ScanScope® and semi-quantitatively analyzed. The percentage of CD3 positive cells to total tumor cells is calculated using Aperio ImageScope software. Results are compared by One Way ANOVA, followed by Holm-Sidak method for multiple comparisons (Sigma Plot 12.5, Systat Software).

In experiments performed as described above, Antibody A1/2 induces CD3+ T cell tumor infiltration in L55 established tumors. The percentage of CD3+ T cells in response to Antibody A1/2 (60%) is higher as compared to BMS20H4.9 (18%) or human IgG (27%) treatments.

Combinations of Antibody A1/2 and Antibody B

Antibody A1/2 in combination with the anti-human PD-L1 antibody, Antibody B, can be tested using the NCI-H292 Winn model, HCC827 human NSCLC model, and the L55 human NSCLC model. The NCI-H292 Winn model is used as follows. Female NOD/SCID Gamma (NSG) mice at 7 weeks age (Jackson Laboratories) are used. Human NSCLC cell line NCI-H292 (ATCC; CRL-1848), cultured in its respective media, is harvested at approximately 80%-90% confluence and suspended in HBSS at $10\times10^6$ cells/mL. Human PBMCs are isolated from a unit of whole blood obtained from NY Blood Center as described previously. The PBMCs are combined with NCI-H292 tumor cells at a 4:1 ratio of tumor cells to PBMC. The mixture is centrifuged and the pellet is re-suspended in HBSS at a concentration of $10\times10^6$ NCI-H292 cells and $2.5\times10^6$ PBMC per mL. Each mouse is implanted subcutaneously on the right flank with 0.2 mL of the solution on Day 0. A control group receiving tumor cells alone is included in each study. Mice are randomly assigned to treatment groups of 5 to 8 mice and treatment commences on Day 0 or Day 1. Treatment groups typically include control IgG, Antibody A1/2, anti-human PD-L1 antibody (Antibody B) and combinations of Antibody A1/2 and Antibody B. Animals are dosed intraperitoneally at 10 mg/kg, unless indicated, once weekly for 4 weeks. Antibody B is dosed at 0.25 mg/kg for the Winn model or 1 mg/kg for the HCC827 model, once weekly for 4 weeks.

The HCC827 human NSCLC (ATCC; CRL-2868) and L55 human NSCLC (University of Pennsylvania) tumor cell lines are maintained in their respective media and harvested for implantation. Tumor cells (cell number range 10×10⁶ for HCC827 (HBSS) and 5×10⁶ for L55 (1:1 HBSS and Matrigel mixture) per mouse) are injected subcutaneously into right flank of female NOD/SCID Gamma (NSG) mice at 7 weeks age (Jackson Laboratories). When tumors reach approximately 250 mm³ to 400 mm³ in size, mice are randomized into groups of 5 to 8 mice. Human expanded T cells are generated as described previously. Expanded T cells (from 3×10⁶ to 8×10⁶) or PBMCs (from 5×10⁵ to 8×10⁶) are thawed and injected into mice. As a control, tumor cells alone are implanted with no T cells or PBMCs. Treatment starts either on Day 0 or Day 1. Treatment groups typically include control IgG, Antibody A1/2, Antibody B, a combination of Antibody A1/2 and Antibody B. Animals are dosed i.p. at 10 mg/kg (unless indicated otherwise) once weekly for 4 weeks.

For all models, body weight (BW) is recorded twice a week and the % change in BW is calculated essentially as described above. Tumor volumes are measured twice per week using electronic calipers and tumor volume is calculated as described above. Additionally, % Regression is calculated using the formula=100×ΔT/T$_{initial}$, if Δ<0. Animals with no measurable tumors are considered as complete responders (CR) and tumors with ≥50% regressions are partial responders (PR). Statistical analysis of tumor volume data is performed with a two-way repeated measures analysis of variance by time and treatment using the MIXED procedures in SAS software (Version 9.2). A Bliss independence analysis is carried out to determine if the effect of combination treatment with two compounds tested is additive or greater than additive or less than additive as compared to either single agent. The percent Response is % Delta T/C for tumor volumes above baseline and % Regression for tumor volumes below baseline. Differences of (single agent treatment)−(combination treatment) are compared. In experiments performed as described, Antibody A1/2 in combination with Antibody B provides an additive tumor growth inhibition relative to monotherapy with Antibody A1/2 or Antibody B, as shown in Table 9.

TABLE 9

| Study | Antibody A1/2 % T/C, p value | Antibody B % T/C, p value | Antibody A1/2 + Antibody B % T/C, p value | Combination vs Antibody A1/2* | Combination vs Antibody B* |
|---|---|---|---|---|---|
| H292 Winn | 74.5, p = 0.419 | 30.9, p = 0.002 | 12.9, p < 0.001 | p < 0.001 | p = 0.052 |
| HCC827 Established | 13, p < 0.001 | 8, p < 0.001 | regression −45% | p < 0.001 | p < 0.001 |
| L55 Established | 99.3, p = 0.832 | 76.6, p = 0.079 | 49.9, p < 0.001 | p < 0.001 | p = 0.003 |

*Bliss Independence Method

Amino Acid and Nucleotide Sequences (human CD137)
SEQ ID NO: 1
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL (HCDR1)
SEQ ID NO: 2
KASGGTFSSYAIS (HCDR2)
SEQ ID NO: 3
GIIPIFGTANYAQKFQG (HCDR3)
SEQ ID NO: 4
ARDLMTTAPGTYFDL (LCDR1)
SEQ ID NO: 5
QASQDIGNSLG (LCDR2)
SEQ ID NO: 6
FDASDLET (LCDR3)
SEQ ID NO: 7
QQGNSFPLT (HCVR)
SEQ ID NO: 8
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARDL

MTTAPGTYFDLWGRGTLVTV (LCVR of Antibody A1)
SEQ ID NO: 9
AIRMTQSPPSLSASVGDRVTITCQASQDIGNSLGWYQQKPGKAPKLVIFD

ASDLETGVPSRFSGSGSGTDFSLTISSLQPEDFATYYCQQGNSFPLTFGQ

GTRLEIK (HC)
SEQ ID NO: 10
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARDL

MTTAPGTYFDLWGRGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKRVEPKSCDKTHTCPPCPAPEAEGAPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPSSIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK (LC of Antibody A1)
SEQ ID NO: 11
AIRMTQSPPSLSASVGDRVTITCQASQDIGNSLGWYQQKPGKAPKLVIFD

ASDLETGVPSRFSGSGSGTDFSLTISSLQPEDFATYYCQQGNSFPLTFGQ

GTRLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC (LCVR of Antibody A2)
SEQ ID NO: 12
IRMTQSPPSLSASVGDRVTITCQASQDIGNSLGWYQQKPGKAPKLVIFDA

SDLETGVPSRFSGSGSGTDFSLTISSLQPEDFATYYCQQGNSFPLTFGQG

TRLEIK (LC of Antibody A2)
SEQ ID NO: 13
IRMTQSPPSLSASVGDRVTITCQASQDIGNSLGWYQQKPGKAPKLVIFDA

SDLETGVPSRFSGSGSGTDFSLTISSLQPEDFATYYCQQGNSFPLTFGQG

TRLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC (DNA of HC)
SEQ ID NO: 14
CAGGTGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACGAATCCACGAGCACAGCCTACATGGAGCTGA

GCAGCCTGAGATCTGAGGACACGGCCGTGTATTACTGTGCGAGAGATCTG

ATGACTACGGCCCCTGGGACGTACTTCGATCTCTGGGGCCGTGGCACCCT

GGTCACTGTCTCCTCAGCTAGCACCAAGGGCCCATCGGTCTTCCCCCTGG

CACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGC

ACTGACCAGCGGCGTGCACACCTTCCCGGCTGTCCTACAGTCCTCAGGAC

TCTACTCCCTCAGCAGCGTGGTGACCGTGCCCTCCAGCAGCTTGGGCACC

CAGACCTACATCTGCAACGTGAATCACAAGCCCAGCAACACCAAGGTGGA

CAAGAGAGTTGAGCCCAAATCTTGTGACAAAACTCACACATGCCCACCGT

GCCCAGCACCTGAAGCCGAGGGGGCACCGTCAGTCTTCCTCTTCCCCCCA

AAACCCAAGGACACCCTCATGATCTCCCGGACCCCTGAGGTCACATGCGT

GGTGGTGGACGTGAGCCACGAAGACCCTGAGGTCAAGTTCAACTGGTATG

TGGACGGCGTGGAGGTGCATAATGCCAAGACAAAGCCGCGGGAGGAGCAG

TACAACAGCACGTACCGTGTGGTCAGCGTCCTCACCGTCCTGCACCAAGA

CTGGCTGAATGGCAAGGAGTACAAGTGCAAGGTCTCCAACAAAGCCCTCC

CATCCTCCATCGAGAAAACCATCTCCAAAGCCAAAGGGCAGCCCCGAGAA

CCACAGGTGTACACCCTGCCCCCATCCCGGGAGGAGATGACCAAGAACCA

AGTCAGCCTGACCTGCCTGGTCAAAGGCTTCTATCCCAGCGACATCGCCG

TGGAGTGGGAGAGCAATGGGCAGCCGGAGAACAACTACAAGACCACGCCT

CCCGTGCTGGACTCCGACGGCTCCTTCTTCCTCTATTCCAAGCTCACCGT

GGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCG

GGCAAATGA (DNA of LC of Antibody A1)
SEQ ID NO: 15
ATGAGGCTGCTGCCTCTGCTGGCCCTCCTGGCCCTGTGGGGCCCAGACCC

AGCCAGAGCCGCCATCCGGATGACCCAGTCTCCACCCTCCCTGTCTGCAT

CTGTAGGAGACAGAGTCACCATCACTTGCCAGGCGAGTCAGGACATTGGC

AACTCTTTAGGTTGGTATCAGCAGAAACCAGGGAAAGCCCCTAAACTCGT

GATCTTCGATGCATCAGATCTGGAAACAGGGGTCCCATCAAGGTTCAGTG

GCAGTGGATCTGGCACAGATTTCAGTCTCACCATCAGCAGCCTGCAGCCT

GAGGATTTTGCAACTTACTATTGTCAACAGGGTAACAGTTTCCCGCTCAC

CTTCGGCCAAGGGACACGACTGGAGATTAAACGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGTTAG (DNA of LC of Antibody A2)
SEQ ID NO: 16
ATGGAGACAGACACACTCCTGCTATGGGTACTGCTGCTCTGGGTTCCAGG

CTCCACCGGCATCCGGATGACCCAGTCTCCACCCTCCCTGTCTGCATCTG

TAGGAGACAGAGTCACCATCACTTGCCAGGCGAGTCAGGACATTGGCAAC

TCTTTAGGTTGGTATCAGCAGAAACCAGGGAAAGCCCCTAAACTCGTGAT

CTTCGATGCATCAGATCTGGAAACAGGGGTCCCATCAAGGTTCAGTGGCA

GTGGATCTGGCACAGATTTCAGTCTCACCATCAGCAGCCTGCAGCCTGAG

GATTTTGCAACTTACTATTGTCAACAGGGTAACAGTTTCCCGCTCACCTT

CGGCCAAGGGACACGACTGGAGATTAAACGAACTGTGGCCGCACCATCTG

TCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAG

AGCAGGACAGCAAGGACAGCACCTACAGCCTCAGCAGCACCCTGACGCTG

AGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGTT

AG (DNA of LC of Antibody A1/2)
SEQ ID NO: 17
ATGGAGACAGACACACTCCTGCTATGGGTACTGCTGCTCTGGGTTCCAGG

CTCCACCGGCGCCATCCGGATGACCCAGTCTCCACCCTCCCTGTCTGCAT

```
CTGTAGGAGACAGAGTCACCATCACTTGCCAGGCGAGTCAGGACATTGGC
AACTCTTTAGGTTGGTATCAGCAGAAACCAGGGAAAGCCCCTAAACTCGT
GATCTTCGATGCATCAGATCTGGAAACAGGGGTCCCATCAAGGTTCAGTG
GCAGTGGATCTGGCACAGATTTCAGTCTCACCATCAGCAGCCTGCAGCCT
GAGGATTTTGCAACTTACTATTGTCAACAGGGTAACAGTTTCCCGCTCAC
CTTCGGCCAAGGGACACGACTGGAGATTAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGT
GTTAG
```

(HC of BMS20H4.9)
                  SEQ ID NO: 18
QVQLQQWGAGLLKPSETLSLTCAVYGGSFSGYYWSWIRQSPEKGLEWIGE
INHGGYVTYNPSLESRVTISVDTSKNQFSLKLSSVTAADTAVYYCARDYG
PGNYDWYFDLWGRGTLVTVSSASTKGPSVFPLAPCSRSTSESTAALGCLV
KDYFPEPVTVSWNSGALTSGVHTFPAVLQSSGLYSLSSVVTVPSSSLGTK
TYTCNVDHKPSNTKVDKRVESKYGPPCPPCPAPEFLGGPSVFLFPPKPKD
TLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK (LC of BMS20H4.9)
                  SEQ ID NO: 19
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPPALTF
GGGTKVEIKRTVAAPSVFIFPPSDEQLKSGTASVVCLLNNFYPREAKVQW
KVDNALQSGNSQESVTEQDSKDSTYSLSSTLTLSKADYEKHKVYACEVTH
QGLSSPVTKSFNRGEC (HC of PF83)
                  SEQ ID NO: 20
EVQLVQSGAEVKKPGESLRISCKGSGYSFSTYWISWVRQMPGKGLEWMGK
IYPGDSYTNYSPSFQGQVTISADKSISTAYLQWSSLKASDTAMYYCARGY
GIFDYWGQGTLVTVSSASTKGPSVFPLAPCSRSTSESTAALGCLVKDYFP
EPVTVSWNSGALTSGVHTFPAVLQSSGLYSLSSVVTVPSSNFGTQTYTCN
VDHKPSNTKVDKTVERKCCVECPPCPAPPVAGPSVFLFPPKPKDTLMISR
TPEVTCVVVDVSHEDPEVQFNWYVDGVEVHNAKTKPREEQFNSTERVVSV
LTVVHQDWLNGKEYKCKVSNKGLPAPIEKTISKTKGQPREPQVYTLPPSR
EEMTKNQVSLTCLVKGFYPSDIAVEWESNGQPEMETDTLLLWVLLLWVPG
STGAIRMTQSPPSLSASVGDRVTITCQASQDIGNSLGWYQQKPGKAPKLV
IFDASDLETGVPSRFSGSGSGTDFSLTISSLQPEDFATYYCQQGNSFPLT
FGQGTRLEIKRTVAAPSVFIFPPSDEQLKSGTASVVCLLNNFYPREAKVQ
WKVDNALQSGNSQESVTEQDSKDSTYSLSSTLTLSKADYEKHKVYACEVT
HQGLSSPVTKSFNRGECNNYKTTPPMLDSDGSFFLYSKLTVDKSRWQQGN
VFSCSVMHEALHNHYTQKSLSLSPGK (LC of PF83)
                  SEQ ID NO: 21
SYELTQPPSVSVSPGQTASITCSGDNIGDQYAHWYQQKPGQSPVLVIYQD
KNRPSGIPERFSGSNSGNTATLTISGTQAMDEADYYCATYTGFGSLAVFG
GGTKLTVLGQPKAAPSVTLFPPSSEELQANKATLVCLISDFYPGAVTVAW
KADSSPVKAGVETTTPSKQSNNKYAASSYLSLTPEQWKSHRSYSCQVTHE
GSTVEKTVAPTECS (HCVR of Antibody B)
                  SEQ ID NO: 22
QVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARSP
DYSPYYYYGMDVWGQGTTVTVSS (LCVR of Antibody B)
                  SEQ ID NO: 23
QSVLTQPPSASGTPGQRVTISCSGSSSNIGSNTVNWYQQLPGTAPKLLIY
GNSNRPSGVPDRFSGSKSGTSASLAISGLQSEDEADYYCQSYDSSLSGSV
FGGGIKLTVLG (HC of Antibody B)
                  SEQ ID NO: 24
QVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCARSP
DYSPYYYYGMDVWGQGTTVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKRVEPKSCDKTHTCPPCPAPEAEGAPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPSSIEKTISKAKGQPR
EPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLS
PGK (LC of Antibody B)
                  SEQ ID NO: 25
QSVLTQPPSASGTPGQRVTISCSGSSSNIGSNTVNWYQQLPGTAPKLLIY
GNSNRPSGVPDRFSGSKSGTSASLAISGLQSEDEADYYCQSYDSSLSGSV
FGGGIKLTVLGQPKAAPSVTLFPPSSEELQANKATLVCLISDFYPGAVTV
AWKADSSPVKAGVETTTPSKQSNNKYAASSYLSLTPEQWKSHRSYSCQVT
HEGSTVEKTVAPAECS (Human PD-L1)
                  SEQ ID NO: 26
MRIFAVFIFMTYWHLLNAFTVTVPKDLYVVEYGSNMTIECKFPVEKQLDLA
ALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHEL
TCQAEGYPKAEVIWTSSDHQVLSGKTTTTNSKREEKLFNVTSTLRINTTTN -continued
EIFYCTFRRLDPEENHTAELVIPELPLAHPPNERTHLVILGAILLCLGVAL

TFIFRLRKGRMMDVKKCGIQDTNSKKQSDTHLEET

---

We claim:

1. A method of treating cancer comprising administering to a patient in need thereof, an effective amount of an anti-human CD137 antibody in combination with an effective amount of an anti-human PD-L1 antibody; wherein the anti-human CD137 antibody comprises HCDR1 having the amino acid sequence of SEQ ID NO: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7.

2. The method of claim 1, wherein the anti-human CD137 antibody comprises a heavy chain variable region having the amino acid sequence of SEQ ID NO: 8 and a light chain variable region having the amino acid sequence of SEQ ID NO: 9.

3. The method of claim 1, wherein the anti-human CD137 antibody comprises a heavy chain variable region having the amino acid sequence of SEQ ID NO: 8 and a light chain variable region having the amino acid sequence of SEQ ID NO: 12.

4. The method of claim 1, wherein the anti-human CD137 antibody comprises a heavy chain having the amino acid sequence of SEQ ID NO: 10 and a light chain having the amino acid sequence of SEQ ID NO: 11.

5. The method of claim 1, wherein the anti-human CD137 antibody comprises a heavy chain having the amino acid sequence of SEQ ID NO: 10 and a light chain having the amino acid sequence of SEQ ID NO: 13.

6. The method of claim 1, wherein the anti-human PD-L1 antibody is atezolizumab, durvalumab, or avelumab.

7. The method of claim 1, wherein the anti-human PD-L1 antibody comprises a heavy chain variable region having the amino acid sequence of SEQ ID NO: 22 and a light chain variable region having the amino acid sequence of SEQ ID NO: 23.

8. The method of claim 1, wherein the anti-human PD-L1 antibody comprises a heavy chain having the amino acid sequence of SEQ ID NO: 24 and a light chain having the amino acid sequence of SEQ ID NO: 25.

9. The method of claim 1, wherein the cancer is bladder cancer, breast cancer, biliary tract cancer, colon cancer, endometrial cancer, esophageal cancer, gastric cancer, head and neck cancer, non-small cell lung cancer, prostate cancer, rectal cancer, or thyroid cancer.

10. The method of claim 1, wherein the cancer is cholangiocarcinoma, head and neck squamous cell carcinoma, lung adenocarcinoma, lung squamous cell carcinoma, or clear cell renal carcinoma.

11. The method of claim 1, wherein the cancer is bladder cancer, head and neck squamous cell carcinoma, or renal cell carcinoma.

12. The method claim 1, wherein at least one of the anti-human CD137 antibody and anti-human PD-L1 antibody is administered in combination with ionizing radiation.

13. The method of claim 1, wherein at least one of the anti-human CD 137 antibody and anti-human PD-L1 antibody is administered in combination with one or more chemotherapeutic agents.

* * * * *

SEQUENCE LISTING

<160> NUMBER OF SEQ ID NOS: 26

<210> SEQ ID NO 1
<211> LENGTH: 255
<212> TYPE: PRT
<213> ORGANISM: Homo sapiens

<400> SEQUENCE: 1

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 2
<211> LENGTH: 13
<212> TYPE: PRT
<213> ORGANISM: Artificial Sequence
<220> FEATURE:
<223> OTHER INFORMATION: synthetic peptide

<400> SEQUENCE: 2

```
Lys Ala Ser Gly Gly Thr Phe Ser Ser Tyr Ala Ile Ser
1               5                   10
```

```
<210> SEQ ID NO 3
<211> LENGTH: 17
<212> TYPE: PRT
<213> ORGANISM: Artificial Sequence
<220> FEATURE:
<223> OTHER INFORMATION: synthetic peptide

<400> SEQUENCE: 3

Gly Ile Ile Pro Ile Phe Gly Thr Ala Asn Tyr Ala Gln Lys Phe Gln
1               5                   10                  15

Gly

<210> SEQ ID NO 4
<211> LENGTH: 15
<212> TYPE: PRT
<213> ORGANISM: Artificial Sequence
<220> FEATURE:
<223> OTHER INFORMATION: synthetic peptide

<400> SEQUENCE: 4

Ala Arg Asp Leu Met Thr Thr Ala Pro Gly Thr Tyr Phe Asp Leu
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Gln Ala Ser Gln Asp Ile Gly Asn Ser Leu Gly
1               5                   10

<210> SEQ ID NO 6
<211> LENGTH: 8
<212> TYPE: PRT
<213> ORGANISM: Artificial Sequence
<220> FEATURE:
<223> OTHER INFORMATION: synthetic peptide

<400> SEQUENCE: 6

Phe Asp Ala Ser Asp Leu Glu Thr
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Gln Gln Gly Asn Ser Phe Pro Leu Thr
1               5

<210> SEQ ID NO 8
<211> LENGTH: 120
<212> TYPE: PRT
<213> ORGANISM: Artificial Sequence
<220> FEATURE:
<223> OTHER INFORMATION: synthetic peptide

<400> SEQUENCE: 8

Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Asp Leu Met Thr Thr Ala Pro Gly Thr Tyr Phe Asp Leu Trp
             100                 105                 110

Gly Arg Gly Thr Leu Val Thr Val
         115                 120

<210> SEQ ID NO 9
<211> LENGTH: 107
<212> TYPE: PRT
<213> ORGANISM: Artificial Sequence
<220> FEATURE:
<223> OTHER INFORMATION: synthetic sequence

<400> SEQUENCE: 9

Ala Ile Arg Met Thr Gln Ser Pro Pro Ser Leu Ser Ala Ser Val Gly
1               5                   10                  15

Asp Arg Val Thr Ile Thr Cys Gln Ala Ser Gln Asp Ile Gly Asn Ser
             20                  25                  30

Leu Gly Trp Tyr Gln Gln Lys Pro Gly Lys Ala Pro Lys Leu Val Ile
         35                  40                  45

Phe Asp Ala Ser Asp Leu Glu Thr Gly Val Pro Ser Arg Phe Ser Gly
     50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln Gln Gly Asn Ser Phe Pro Leu
                 85                  90                  95

Thr Phe Gly Gln Gly Thr Arg Leu Glu Ile Lys
             100                 105

<210> SEQ ID NO 10
<211> LENGTH: 452
<212> TYPE: PRT
<213> ORGANISM: Artificial Sequence
<220> FEATURE:
<223> OTHER INFORMATION: synthetic sequence

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

```
Ala Arg Asp Leu Met Thr Thr Ala Pro Gly Thr Tyr Phe Asp Leu Trp
            100                 105                 110
Gly Arg Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
            165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Arg Val Glu Pro Lys Ser
            210                 215                 220
Cys Asp Lys Thr His Thr Cys Pro Pro Cys Pro Ala Pro Glu Ala Glu
225                 230                 235                 240
Gly Ala Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ser Ser
            325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly Lys
        450

<210> SEQ ID NO 11
<211> LENGTH: 214
<212> TYPE: PRT
<213> ORGANISM: Artificial Sequence
<220> FEATURE:
<223> OTHER INFORMATION: synthetic sequence

<400> SEQUENCE: 11
```

```
Ala Ile Arg Met Thr Gln Ser Pro Pro Ser Leu Ser Ala Ser Val Gly
1               5                   10                  15

Asp Arg Val Thr Ile Thr Cys Gln Ala Ser Gln Asp Ile Gly Asn Ser
                20                  25                  30

Leu Gly Trp Tyr Gln Gln Lys Pro Gly Lys Ala Pro Lys Leu Val Ile
            35                  40                  45

Phe Asp Ala Ser Asp Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65              70                  75                  80

Glu Asp Phe Ala Thr Tyr Tyr Cys Gln Gln Gly Asn Ser Phe Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 106
<212> TYPE: PRT
<213> ORGANISM: Artificial Sequence
<220> FEATURE:
<223> OTHER INFORMATION: synthetic sequence

<400> SEQUENCE: 12

Ile Arg Met Thr Gln Ser Pro Pro Ser Leu Ser Ala Ser Val Gly Asp
1               5                   10                  15

Arg Val Thr Ile Thr Cys Gln Ala Ser Gln Asp Ile Gly Asn Ser Leu
                20                  25                  30

Gly Trp Tyr Gln Gln Lys Pro Gly Lys Ala Pro Lys Leu Val Ile Phe
            35                  40                  45

Asp Ala Ser Asp Leu Glu Thr Gly Val Pro Ser Arg Phe Ser Gly Ser
    50                  55                  60

Gly Ser Gly Thr Asp Phe Ser Leu Thr Ile Ser Ser Leu Gln Pro Glu
65              70                  75                  80

Asp Phe Ala Thr Tyr Tyr Cys Gln Gln Gly Asn Ser Phe Pro Leu Thr
                85                  90                  95

Phe Gly Gln Gly Thr Arg Leu Glu Ile Lys
            100                 105

<210> SEQ ID NO 13
<211> LENGTH: 213
<212> TYPE: PRT
<213> ORGANISM: Artificial Sequence
```

<220> FEATURE:
<223> OTHER INFORMATION: synthetic sequence

<400> SEQUENCE: 13

```
Ile Arg Met Thr Gln Ser Pro Ser Leu Ser Ala Ser Val Gly Asp
1               5                   10                  15
Arg Val Thr Ile Thr Cys Gln Ala Ser Gln Asp Ile Gly Asn Ser Leu
                20                  25                  30
Gly Trp Tyr Gln Gln Lys Pro Gly Lys Ala Pro Lys Leu Val Ile Phe
            35                  40                  45
Asp Ala Ser Asp Leu Glu Thr Gly Val Pro Ser Arg Phe Ser Gly Ser
        50                  55                  60
Gly Ser Gly Thr Asp Phe Ser Leu Thr Ile Ser Ser Leu Gln Pro Glu
65                  70                  75                  80
Asp Phe Ala Thr Tyr Tyr Cys Gln Gln Gly Asn Ser Phe Pro Leu Thr
                85                  90                  95
Phe Gly Gln Gly Thr Arg Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 14
<211> LENGTH: 1359
<212> TYPE: DNA
<213> ORGANISM: Artificial Sequence
<220> FEATURE:
<223> OTHER INFORMATION: synthetic sequence

<400> SEQUENCE: 14

```
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagatctg    300
atgactacgg cccctgggac gtacttcgat ctctggggcc gtggcaccct ggtcactgtc    360
tcctcagcta gcaccaaggg cccatcggtc ttccccctgg cacccctcct caagagcacc    420
tctgggggca gcggccct gggctgcctg gtcaaggact acttcccga accggtgacg    480
gtgtcgtgga actcaggcgc actgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagagagtt    660
```

| | |
|---|---|
| gagcccaaat cttgtgacaa aactcacaca tgcccaccgt gcccagcacc tgaagccgag | 720 |
| ggggcaccgt cagtcttcct cttcccccca aacccaagg acaccctcat gatctcccgg | 780 |
| acccctgagg tcacatgcgt ggtggtggac gtgagccacg aagaccctga ggtcaagttc | 840 |
| aactggtatg tggacggcgt ggaggtgcat aatgccaaga caaagccgcg ggaggagcag | 900 |
| tacaacagca cgtaccgtgt ggtcagcgtc ctcaccgtcc tgcaccaaga ctggctgaat | 960 |
| ggcaaggagt acaagtgcaa ggtctccaac aaagccctcc catcctccat cgagaaaacc | 1020 |
| atctccaaag ccaaagggca gccccgagaa ccacaggtgt acaccctgcc cccatcccgg | 1080 |
| gaggagatga ccaagaacca gtcagcctg acctgcctgg tcaaaggctt ctatcccagc | 1140 |
| gacatcgccg tggagtggga gagcaatggg cagccggaga caactacaa gaccacgcct | 1200 |
| cccgtgctgg actccgacgg ctccttcttc ctctattcca agctcaccgt ggacaagagc | 1260 |
| aggtggcagc aggggaacgt cttctcatgc tccgtgatgc atgaggctct gcacaaccac | 1320 |
| tacacgcaga agagcctctc cctgtctccg ggcaaatga | 1359 |

<210> SEQ ID NO 15
<211> LENGTH: 645
<212> TYPE: DNA
<213> ORGANISM: Artificial Sequence
<220> FEATURE:
<223> OTHER INFORMATION: synthetic sequence

<400> SEQUENCE: 15

| | |
|---|---|
| atgaggctgc tgcctctgct ggccctcctg ccctgtgggg cccagaccc agccagagcc | 60 |
| gccatccgga tgacccagtc tccaccctcc ctgtctgcat ctgtaggaga cagagtcacc | 120 |
| atcacttgcc aggcgagtca ggacattggc aactctttag gttggtatca gcagaaacca | 180 |
| gggaaagccc ctaaactcgt gatcttcgat gcatcagatc tggaaacagg gtcccatca | 240 |
| aggttcagtg gcagtggatc tggcacagat ttcagtctca ccatcagcag cctgcagcct | 300 |
| gaggattttg caacttacta ttgtcaacag ggtaacagtt tcccgctcac cttcggccaa | 360 |
| gggacacgac tggagattaa acgaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga aaacacaaa gtctacgcct gcgaagtcac ccatcagggc | 600 |
| ctgagctcgc ccgtcacaaa gagcttcaac aggggagagt gttag | 645 |

<210> SEQ ID NO 16
<211> LENGTH: 702
<212> TYPE: DNA
<213> ORGANISM: Artificial Sequence
<220> FEATURE:
<223> OTHER INFORMATION: synthetic sequence

<400> SEQUENCE: 16

| | |
|---|---|
| atggagacag acacactcct gctatgggta ctgctgctct gggttccagg ctccaccggc | 60 |
| atccggatga cccagtctcc accctccctg tctgcatctg taggagacag agtcaccatc | 120 |
| acttgccagg cgagtcagga cattggcaac tctttaggtt ggtatcagca gaaaccaggg | 180 |
| aaagcccta aactcgtgat cttcgatgca tcagatctgg aaacagggt cccatcaagg | 240 |
| ttcagtggca gtggatctgg cacagattc agtctcacca tcagcagcct gcagcctgag | 300 |
| gattttgcaa cttactattg tcaacagggt aacagtttcc cgctcacctt cggccaaggg | 360 |
| acacgactgg agattaaacg aactgtggcc gcaccatctg tcttcatctt cccgccatct | 420 |

```
gatgagcagt tgaaatctgg aactgcctct gttgtgtgcc tgctgaataa cttctatccc    480
agagaggcca aagtacagtg aaggtggat  aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ag                      702
```

<210> SEQ ID NO 17
<211> LENGTH: 705
<212> TYPE: DNA
<213> ORGANISM: Artificial Sequence
<220> FEATURE:
<223> OTHER INFORMATION: synthetic sequence

<400> SEQUENCE: 17

```
atggagacag acacactcct gctatgggta ctgctgctct gggttccagg ctccaccggc    60
gccatccgga tgacccagtc tccaccctcc ctgtctgcat ctgtaggaga cagagtcacc    120
atcacttgcc aggcgagtca ggacattggc aactctttag gttggtatca gcagaaacca    180
gggaaagccc ctaaactcgt gatcttcgat gcatcagatc tggaaacagg gtcccatca    240 aggttcagtg gcagtggatc tggcacagat ttcagtctca ccatcagcag cctgcagcct    300
gaggattttg caacttacta ttgtcaacag ggtaacagtt cccgctcac  cttcggccaa    360 gggacacgac tggagattaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca gagcagga   cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                   705
```

<210> SEQ ID NO 18
<211> LENGTH: 448
<212> TYPE: PRT
<213> ORGANISM: Artificial Sequence
<220> FEATURE:
<223> OTHER INFORMATION: synthetic sequence

<400> SEQUENCE: 18

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125
```

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 19
<211> LENGTH: 216
<212> TYPE: PRT
<213> ORGANISM: Artificial Sequence
<220> FEATURE:
<223> OTHER INFORMATION: synthetic sequence

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

```
Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 20
<211> LENGTH: 676
<212> TYPE: PRT
<213> ORGANISM: Artificial Sequence
<220> FEATURE:
<223> OTHER INFORMATION: synthetic sequence

<400> SEQUENCE: 20

Glu Val Gln Leu Val Gln Ser Gly Ala Glu Val Lys Lys Pro Gly Glu
 1               5                  10                  15

Ser Leu Arg Ile Ser Cys Lys Gly Ser Gly Tyr Ser Phe Ser Thr Tyr
             20                  25                  30

Trp Ile Ser Trp Val Arg Gln Met Pro Gly Lys Gly Leu Glu Trp Met
         35                  40                  45

Gly Lys Ile Tyr Pro Gly Asp Ser Tyr Thr Asn Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190
```

```
Gly Thr Gln Thr Tyr Thr Cys Asn Val Asp His Lys Pro Ser Asn Thr
            195                 200                 205

Lys Val Asp Lys Thr Val Glu Arg Lys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
            245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
            290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Met
370                 375                 380

Glu Thr Asp Thr Leu Leu Leu Trp Val Leu Leu Leu Trp Val Pro Gly
385                 390                 395                 400

Ser Thr Gly Ala Ile Arg Met Thr Gln Ser Pro Pro Ser Leu Ser Ala
                405                 410                 415

Ser Val Gly Asp Arg Val Thr Ile Thr Cys Gln Ala Ser Gln Asp Ile
                420                 425                 430

Gly Asn Ser Leu Gly Trp Tyr Gln Gln Lys Pro Gly Lys Ala Pro Lys
            435                 440                 445

Leu Val Ile Phe Asp Ala Ser Asp Leu Glu Thr Gly Val Pro Ser Arg
450                 455                 460

Phe Ser Gly Ser Gly Ser Gly Thr Asp Phe Ser Leu Thr Ile Ser Ser
465                 470                 475                 480

Leu Gln Pro Glu Asp Phe Ala Thr Tyr Tyr Cys Gln Gln Gly Asn Ser
                485                 490                 495

Phe Pro Leu Thr Phe Gly Gln Gly Thr Arg Leu Glu Ile Lys Arg Thr
            500                 505                 510

Val Ala Ala Pro Ser Val Phe Ile Phe Pro Pro Ser Asp Glu Gln Leu
            515                 520                 525

Lys Ser Gly Thr Ala Ser Val Val Cys Leu Leu Asn Asn Phe Tyr Pro
530                 535                 540

Arg Glu Ala Lys Val Gln Trp Lys Val Asp Asn Ala Leu Gln Ser Gly
545                 550                 555                 560

Asn Ser Gln Glu Ser Val Thr Glu Gln Asp Ser Lys Asp Ser Thr Tyr
                565                 570                 575

Ser Leu Ser Ser Thr Leu Thr Leu Ser Lys Ala Asp Tyr Glu Lys His
            580                 585                 590

Lys Val Tyr Ala Cys Glu Val Thr His Gln Gly Leu Ser Ser Pro Val
            595                 600                 605

Thr Lys Ser Phe Asn Arg Gly Glu Cys Asn Asn Tyr Lys Thr Thr Pro
```

```
                        610                 615                 620
Pro Met Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
                660                 665                 670

Ser Pro Gly Lys
        675

<210> SEQ ID NO 21
<211> LENGTH: 214
<212> TYPE: PRT
<213> ORGANISM: Artificial Sequence
<220> FEATURE:
<223> OTHER INFORMATION: synthetic sequence

<400> SEQUENCE: 21

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 22
<211> LENGTH: 123
<212> TYPE: PRT
<213> ORGANISM: Artificial Sequence
<220> FEATURE:
<223> OTHER INFORMATION: synthetic sequence

<400> SEQUENCE: 22

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Thr Phe Ser Ser Tyr
                20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Pro Asp Tyr Ser Pro Tyr Tyr Tyr Gly Met Asp Val
            100                 105                 110

Trp Gly Gln Gly Thr Thr Val Thr Val Ser Ser
            115                 120

<210> SEQ ID NO 23
<211> LENGTH: 111
<212> TYPE: PRT
<213> ORGANISM: Artificial Sequence
<220> FEATURE:
<223> OTHER INFORMATION: synthetic sequence

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly
            100                 105                 110

<210> SEQ ID NO 24
<211> LENGTH: 453
<212> TYPE: PRT
<213> ORGANISM: Artificial Sequence
<220> FEATURE:
<223> OTHER INFORMATION: synthetic sequence

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Ser Pro Asp Tyr Ser Pro Tyr Tyr Tyr Gly Met Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Glu Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 25
<211> LENGTH: 216
<212> TYPE: PRT
<213> ORGANISM: Artificial Sequence
<220> FEATURE:
<223> OTHER INFORMATION: synthetic sequence

<400> SEQUENCE: 25
```

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Ile Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Ala Glu Cys Ser
    210                 215

<210> SEQ ID NO 26
<211> LENGTH: 290
<212> TYPE: PRT
<213> ORGANISM: Artificial Sequence
<220> FEATURE:
<223> OTHER INFORMATION: synthetic sequence

<400> SEQUENCE: 26

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140
```

```
Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290
```